United States Patent [19]
Coleman et al.

[11] Patent Number: 5,628,744
[45] Date of Patent: May 13, 1997

[54] TREATMENT BEAM HANDPIECE

[75] Inventors: Tony D. Coleman, San Jose; Scott A. Davenport, Half Moon Bay, both of Calif.

[73] Assignee: Laserscope, San Jose, Calif.

[21] Appl. No.: 171,593

[22] Filed: Dec. 21, 1993

[51] Int. Cl.⁶ .................................................. A61B 17/36
[52] U.S. Cl. ........................ 606/12; 606/10; 606/2; 606/13; 607/89
[58] Field of Search ................................ 606/2, 3, 7, 9, 606/10–13, 17; 607/88, 89

[56] References Cited

U.S. PATENT DOCUMENTS

| | | | |
|---|---|---|---|
| 4,316,467 | 2/1982 | Muckerhelpe | 606/9 |
| 4,768,513 | 9/1988 | Suzuki | 606/9 |
| 5,071,417 | 12/1991 | Sinorsky | 606/10 |
| 5,275,594 | 1/1994 | Baker et al. | 606/10 |
| 5,334,191 | 8/1994 | Poppas et al. | 606/12 |
| 5,350,376 | 9/1994 | Brown | 606/10 |

OTHER PUBLICATIONS

Feather et al., "A portable reflectometer for the rapid quantification of cutaneous haemoglobin and melanin", Phys. Med. Biol., 1988, vol. 33, No. 6, 711–722.

Tang et al., "In Vivo Spectrophotometric Evaluation of Normal, Lesional, and Laser–Treated Skin in Patients with Port–Wine Stains", The Journal of Investigative Dermatology, 80:420–423, 1983.

Pickering, et al. "Copper vapour laser treatment of port–wine stains and other vascular malformations", British Journal of Plastic Surgery (1990), 43:273–282.

*Primary Examiner*—Angela D. Sykes
*Assistant Examiner*—Michael Peffley
*Attorney, Agent, or Firm*—Oblon, Spivak, MacClelland, Maier & Neustadt P.C.

[57] ABSTRACT

A dermatology handpiece delivers a treatment beam of optical energy to a lesion. The handpiece has the ability to selectively determine whether or not the treatment beam is delivering optical energy to a lesion or to healthy tissue. This is achieved without visual inspection of the skin surface by the physician. Slight variations in tissue, not readily discernable by the human eye, can be detected and treated. A base line, or threshold, is established for the treatment area. Normal tissue, falling below the base line, does not receive a dose of optical energy. A threshold or base line signal is created by taking a reading of healthy skin. The dermatology handpiece is adjusted so that the treatment beam is not delivered until a threshold or base line signal is exceeded. Substantially all of a lesion receives the proper amount of optical energy in the treatment beam, while healthy tissue does not receive a dosage of optical energy.

9 Claims, 5 Drawing Sheets

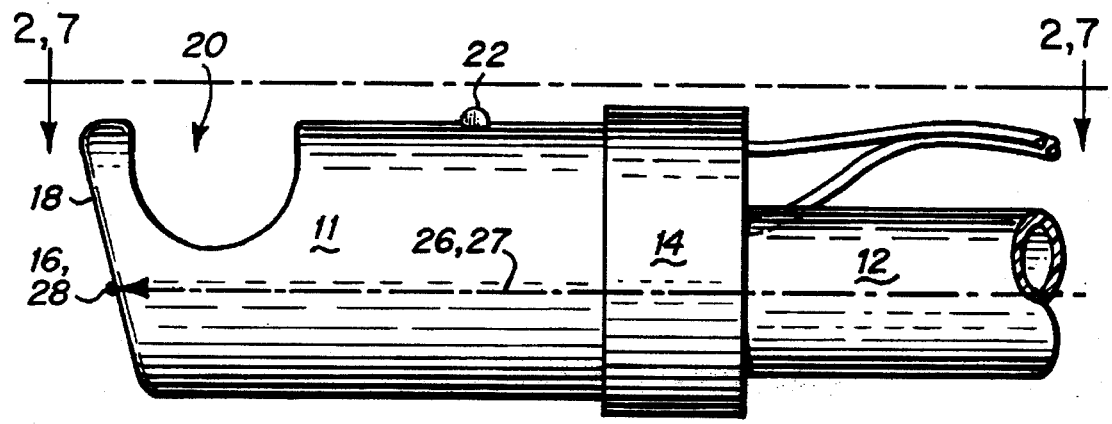
Fig_1
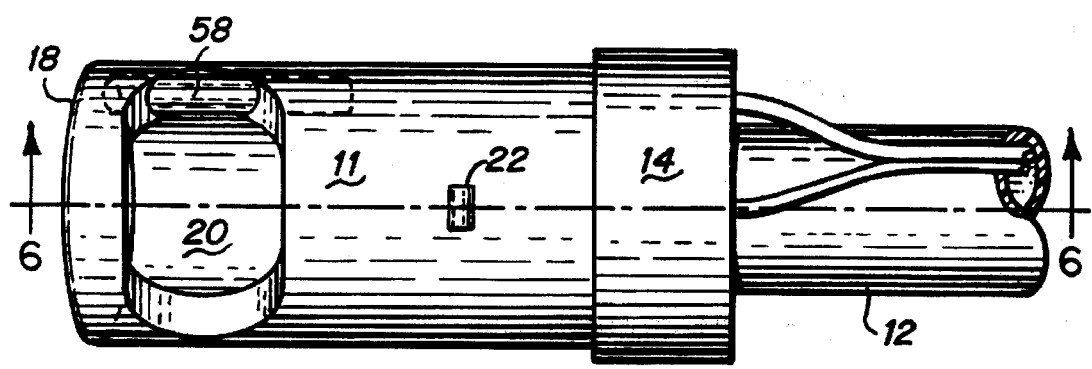
Fig_2

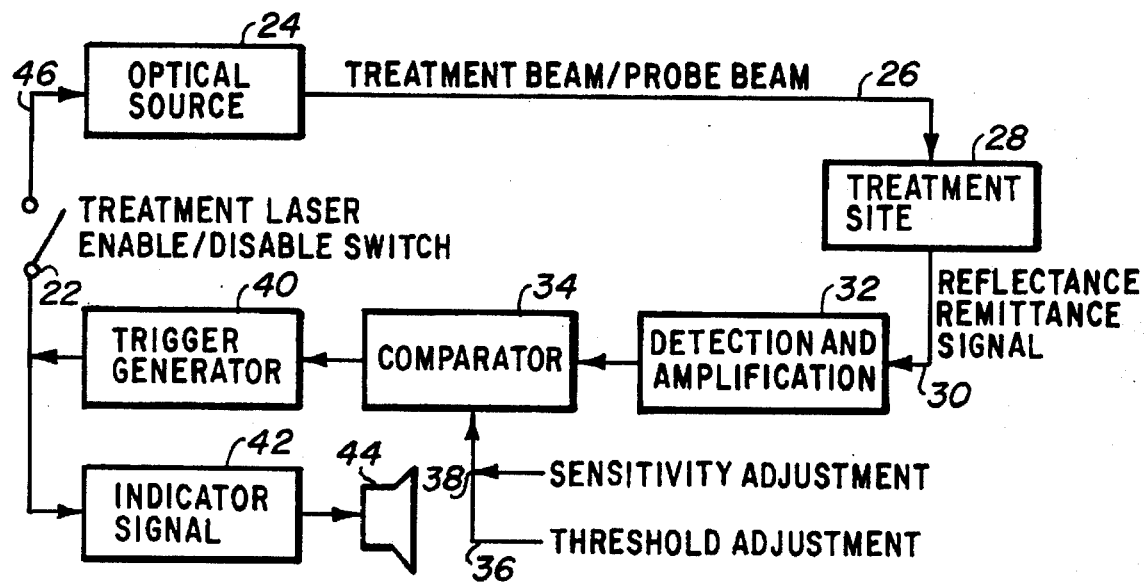
Fig_3
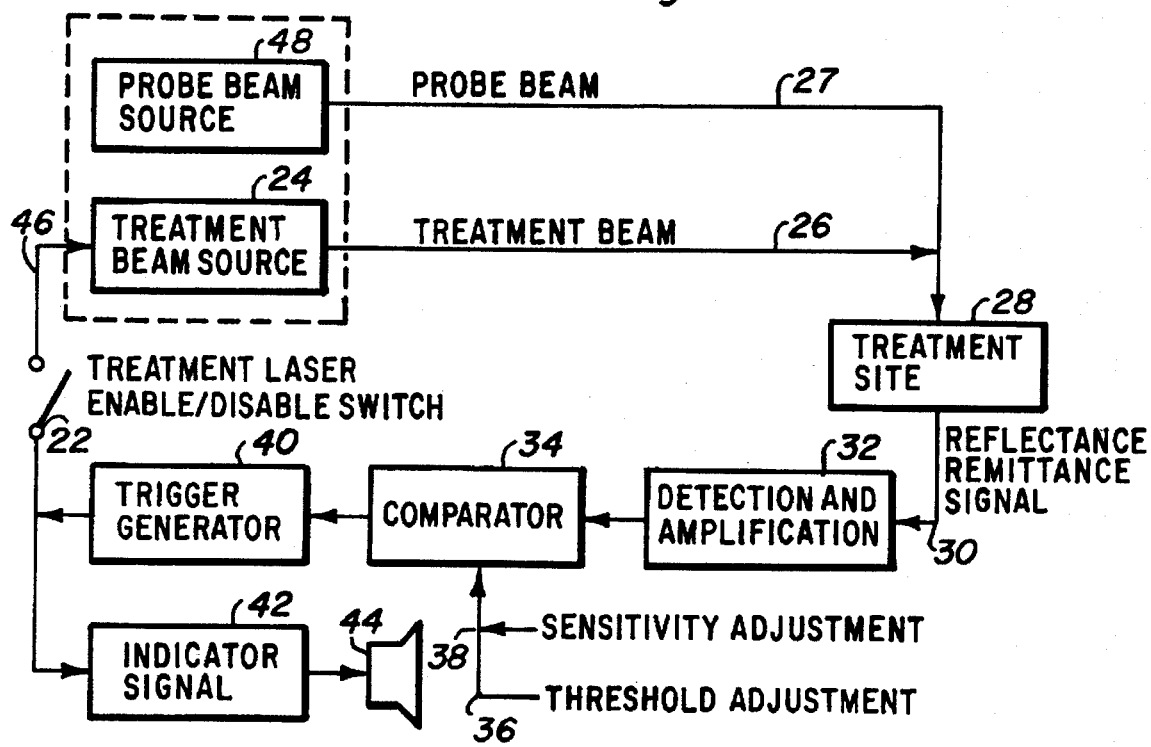
Fig_4

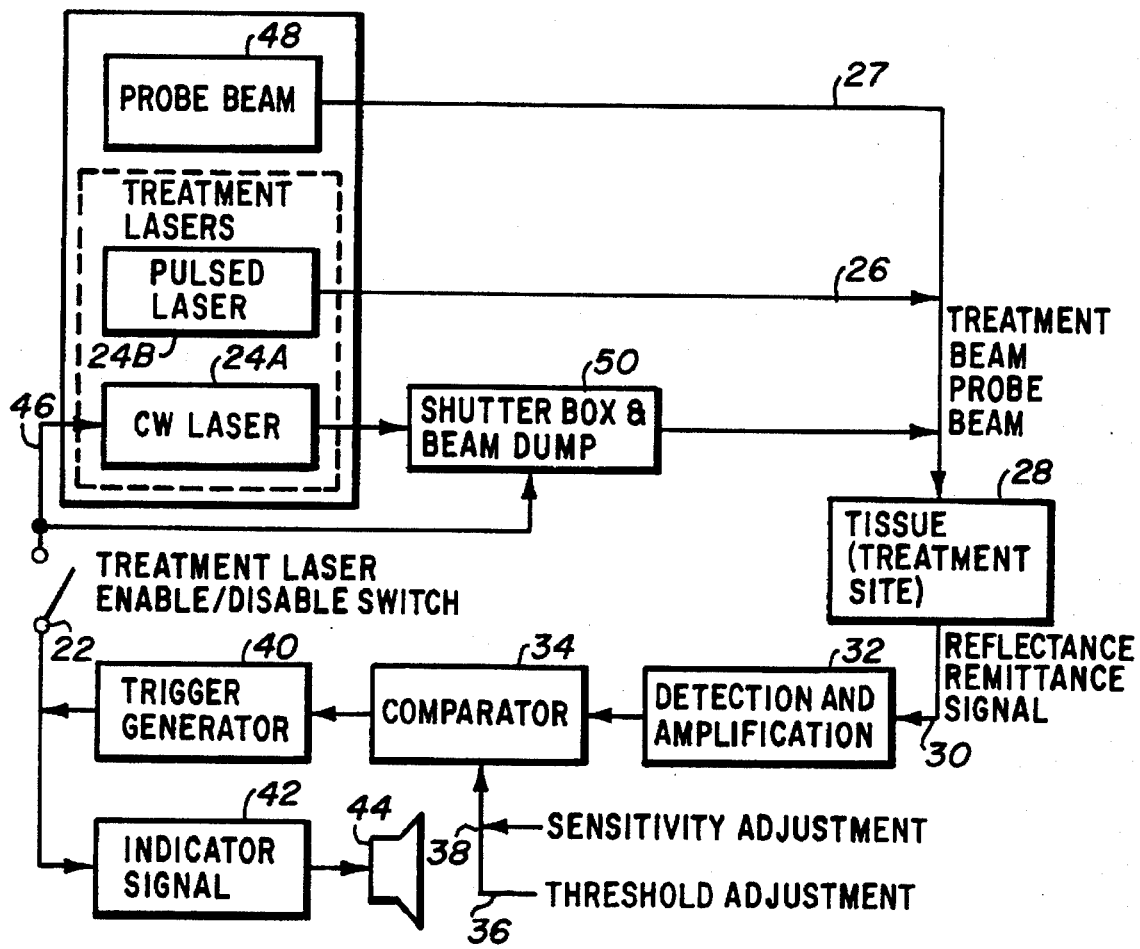
Fig_5
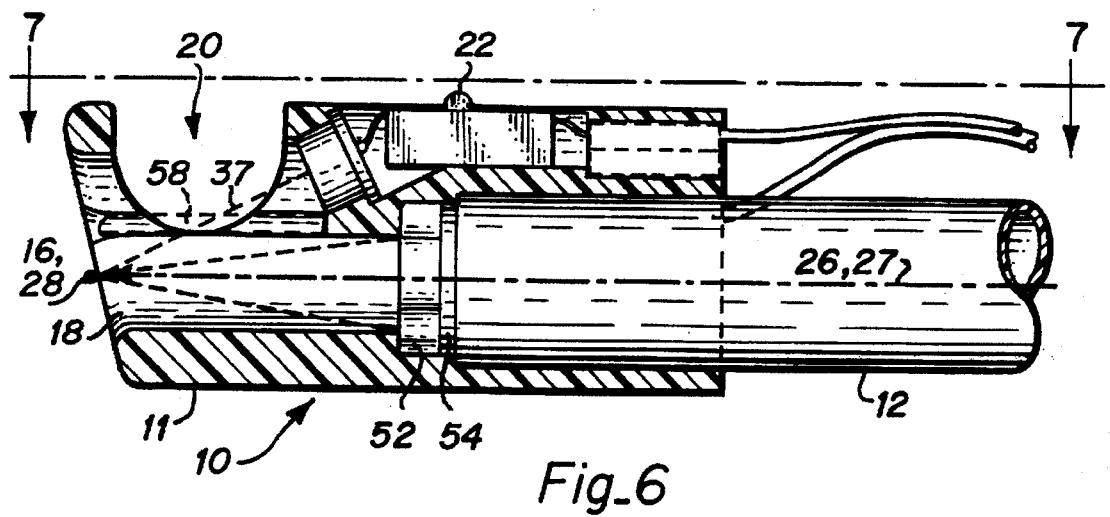
Fig_6

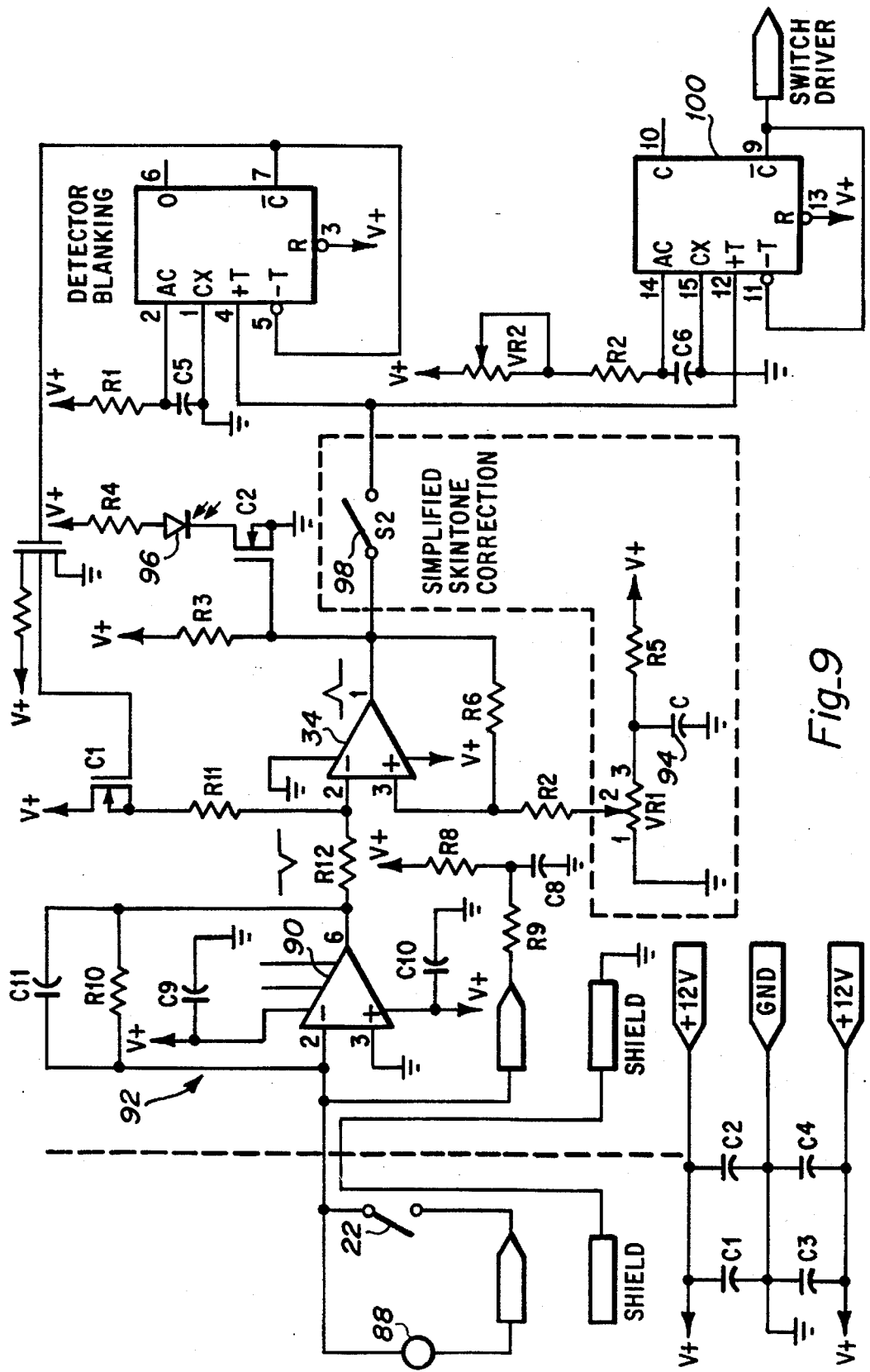
Fig_9

TREATMENT BEAM HANDPIECE

FIELD OF THE INVENTION

This invention relates generally to devices that deliver energy to a treatment site, and more particularly, a dermatology handpiece for treating contrasting pigments in the skin.

BACKGROUND OF THE INVENTION

Lasers have found utility in the treatment of skin lesions such as port wine stains and telangiectasia. They exert their effects on tissue when the high-intensity incident beam of photons is absorbed by a pigment, chromophore, with an appropriate absorption spectrum, releasing heat at the site of this photo-thermal interaction.

Laser wavelengths that are absorbed by target tissues, with the intent to leave surrounding tissues unaffected, improve the specificity of laser treatments. For treatment areas with complicated geometries one technique is to irradiate a large area of the lesion. Tissue absorption characteristics are used to deposit the laser energy in the desired location. This is, however, difficult because the difference in absorption between the target and surrounding tissue varies with each patient. An alternative is for the physician to track the target by following the outline of the treatment area by hand, thereby leaving the surrounding tissue unaffected. Some targets are too small to be lased by such a manual tracking technique. Complicated scanning mechanisms and impractical robotic schemes have been proposed and built to facilitate the laser treatment process. These have proven to be too expensive and clumsy to use.

There are commercial products which deliver laser energy to an area to be treated. Such devices usually indiscriminately deliver laser energy to an area regardless of the need for treatment. This is determined visually by the physician. Discrimination between contrasting dermatological tissue is achieved visually and often is imprecise.

Cutaneous spectrophotometry, a technique that measures reflected monochromatic light from skin, has been employed as a noninvasive method to characterize in vivo pigments on port wine stains, S. V. Tang, et al., *The Journal of Investigative Dermatology*, 1983, 80, pages 420 to 423.

Port wine stains have been treated with yellow 578 nm light from a copper vapor laser. In one instance light was applied by scanning a 1 mm optical fiber approximately 2 mm above a lesion. A maximum scan rate of 3s/cm2 was used, J. W. Pickering, et al., *British Journal of Plastic Surgery*, 1990, 43, pages 273 to 282. Each patient was assigned to a particular class of vascular abnormality. The periphery of the area to be treated was marked with a green pen which contrasted with the color of the lesion. The green outline provided a finishing point for the scan because the true edge of the lesion was not easily discerned.

The color of healthy skin is determined largely by the quantity and degree of oxygenation of blood in the dermis and the presence or absence of the brown/black epidermal pigment, melanin. A specially designed skin reflectance spectrophotometer, the Haemelometer, has been developed for the quantification of cutaneous hemoglobin and melanin by Feather et al., *Phys. Med. Biol.*, 1988. Vol. 33, No. 6, pages 711 to 722. The Haemelometer consists of a power supply, an electronic drive with signal processing capability and a skin reflectance measuring head. Nine LED's and a silicon photodiode detector are positioned in a hollow hemisphere measuring head. Reflectance signals generated in the silicon photodiode detector are amplified and separated into three channels, corresponding to each of three wavelengths. The measuring head is held lightly over an area of skin being studied and provides simultaneous measurement of the hemoglobin and melanin indices.

None of the preceding devices or methods provide a dermatology handpiece which establishes a threshold signal to differentiate between normal skin tissue and a lesion in such a manner that a treatment beam of optical energy is delivered only when the threshold signal is exceeded. Current devices do not provide selectivity between normal tissue and the lesion, other than by visual inspection. Such devices deliver optical energy to lesions and normal tissue without distinguishing between the two.

SUMMARY OF THE INVENTION

The present invention is a dermatology handpiece that delivers a treatment beam of optical energy to a lesion. An optical delivery device is positioned at least partially in a housing. The optical delivery device receives the treatment beam from an optical light source. A treatment beam selectivity device is responsive to the optical delivery device. It provides selective delivery of the treatment beam to the lesion in response to a reflectance signal from a reflectance beam that is reflected from the lesion. The treatment beam delivers optical energy only when it is positioned above the lesion and not over healthy tissue.

The ability to selectively determine whether or not the treatment beam is delivering optical energy to a lesion or to healthy tissue is significant. With prior devices the physician has relied on his or her visual inspection of the skin surface to activate the dermatology handpiece. This results in an imprecise delivery of optical energy to tissue. Slight variations in the appearance of the tissue are not readily discernable by the human eye.

In one embodiment of the present invention, a threshold signal is created by taking a reading of healthy skin with a low power probe beam. The dermatology handpiece is adjusted so that the treatment beam is not delivered until the threshold signal is exceeded. Both the treatment and probe beams are in the same general location but the probe beam has a different wavelength. When the physician treats the lesion the treatment beam is turned on and off, depending on whether or not a reflectance beam, received from the precise site where the treatment beam will be delivered in the next sequence, exceeds the threshold. This maximizes the effective treatment of the lesion. Substantially all of the lesion receives the proper amount of optical energy in the treatment beam, while healthy tissue does not receive a dosage of optical energy.

The present invention is particularly useful in treating a wide variety of individuals, each with different levels of melanin. The threshold signal is determined based on the level of melanin present in each individual patient. There is no set threshold signal that is employed for everyone. The present invention takes into consideration the fact that individuals have different levels of melanin present, and hence, the determination as to whether or not a lesion is present is based upon a prior measurement of that individual's healthy skin melanin content.

Additionally, the present invention can be used to treat only certain lesions. A patient may have a variety of lesions with varying degrees of severity. It may desirable to only treat the most severe lesions. With the present invention, the physician can select a particular class of lesion, based on melanin or hemoglobin content. Again, a significant of selectivity is provided.

Thus, the present invention enables the physician to accurately distinguish between lesions and healthy tissue. The present invention recognizes that individual pigments and hemoglobin contents differ and that there is not one set threshold suitable for all patients. Additionally, the invention permits the physician to treat only certain lesions, depending on their degree of severity.

DESCRIPTION OF THE DRAWINGS

FIG. 1 is a side perspective view of the dermatology handpiece.

FIG. 2 is a top perspective view of the dermatology handpiece.

FIG. 3 is a block diagram of the dermatology handpiece system with a single optical source.

FIG. 4 is a block diagram of the dermatology handpiece system with different probe beam and treatment beam optical sources.

FIG. 5 is a block diagram of the dermatology handpiece system with pulsed and CW laser treatment beam sources.

FIG. 6 is a side sectional view of the handpiece illustrated in FIG. 1.

FIG. 9 is a circuit diagram for the dermatology handpiece system.

DESCRIPTION OF THE PREFERRED EMBODIMENTS

Figure 7:
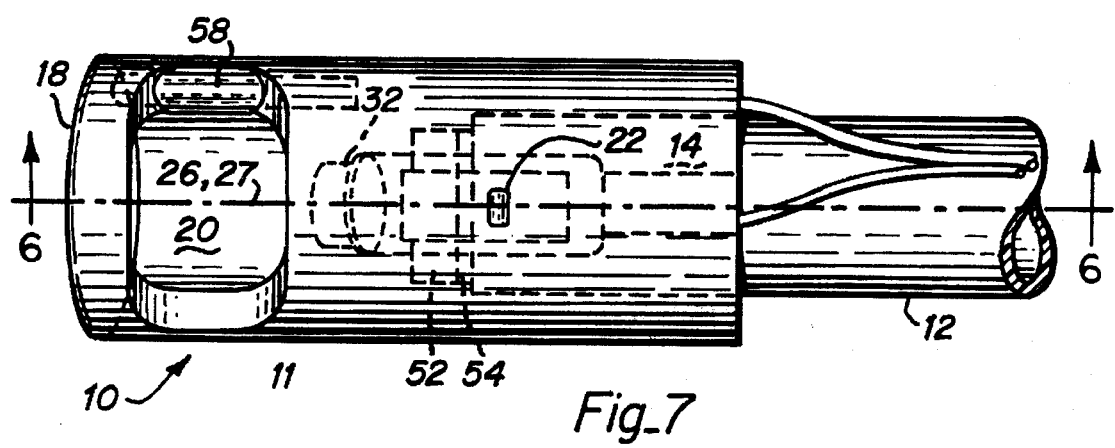
FIG. 7 is a top sectional view of the handpiece illustrated in FIG. 2.
Figure 8:
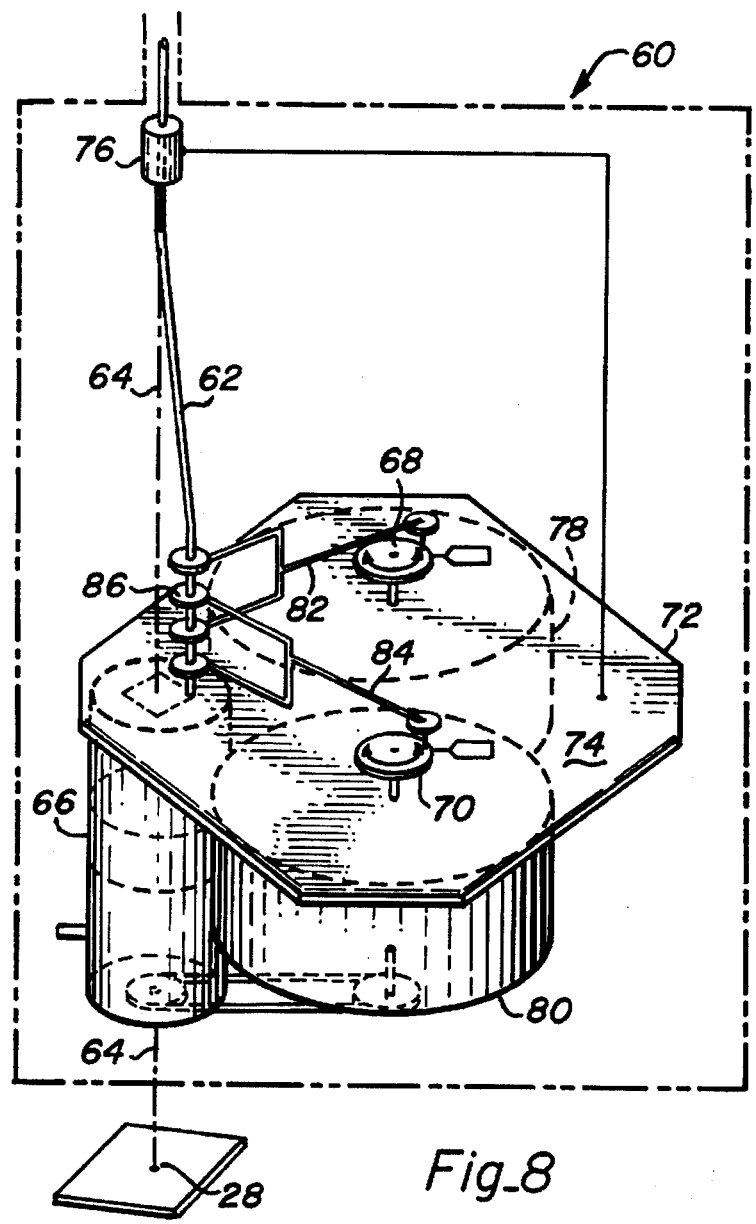
FIG. 8 is a diagram illustrating a scanning system that can be used with the dermatology handpiece.

FIGS. 1 and 2 illustrate exterior views of a dermatology handpiece 10. A cannula 11 retains a dermatology delivery device 12, such as the MicronSpot Handpiece, commercially available from Laserscope, San Jose, Calif. A scanning system, not illustrated in FIGS. 1 or 2, is positioned within housing 14. The scanning system, as will be more fully explained later, provides movement of an optical fiber that delivers optical energy from a laser source to a dermatology lesion.

Dermatology delivery device 12 is connected optically, either directly or indirectly, to a laser source, not shown. A variety of laser sources can be used with the dermatology handpiece of the invention, including but not limited to the following KTP 532/YAG, copper vapor, flash lamp dye, argon, krypton, dye and YAG. Additionally, a concentrated light source, such as an arc lamp, can be used. A focused beam of optical energy 16 emerges from a distal end 18 of cannula 11. A window 20 is formed at distal end 18 and provides the ability to view by the physician. A switch 22 is hand activated by the physician to turn the optical energy from the dermatology handpiece on or off.

FIGS. 3, 4 and 5 illustrate further elements of the invention. Optical source 24 is preferably a laser, and more particularly a KTP 532 wavelength laser. Optical source 24 produces a beam 26 of optical energy. The embodiment shown in FIG. 3 has optical source 24 producing both a treatment beam 26 which is delivered to a tissue site, and a probe beam 27 (FIG. 4). Probe beam 27 is used to establish a threshold value. When the threshold value is exceeded then treatment beam 26 delivers beam 26 to a treatment site 28. Probe beam 27 and treatment beam 26 can be of different wavelengths. For example, probe beam can be in the yellow region of the spectrum, created from a HeNe laser, while the source of treatment beam 26 may by an IR laser. However, both beams are preferably delivered along the same optical fiber, or alternatively, different fibers may be employed.

Treatment site 28 is preferably a dermatology lesion. It can also be portwine stains, tattoos, spider veins, telangiectasias, angiokeratomas, hair removal, application in photo dynamic therapy detection and for the treatment of skin cancer. Beam 26 is reflected from treatment site 28 and produces a reflectance/remittance signal 30 that is received at a detector 32 and amplified. A suitable detector is any photo cell, photo detector/fluorescence detector or photo diodes. One detector that can be used is a Model No. DT 25, commercially available from EG&G.

A signal is produced at detector 32. It is then compared at comparator 34 with a threshold signal that is pre-set by the physician by a threshold adjustment 36 and a sensitivity adjustment 38. Probe beam 27 is reflected from treatment site 28 and reflectance/remittance signal 30 is generated. In setting up the treatment procedure the physician will take a base line reading on healthy or normal tissue. Sensitivity and threshold adjustments 38 and 36 are set by the physician so that healthy tissue, or tissue representative of a person's normal pigment, is set to a base line of "0". Above the base line the treatment beam 26 will deliver optical energy to treatment site 28. Below the base line treatment beam 26 is not activated. Probe beam 37 also provides a method of tracing the delivery of the optical energy.

Alternatively, the physician places dermatology handpiece 10 on normal skin near treatment site 28. Dermatology handpiece 10 is then calibrated by scanning to look at the reflectance of probe beam 27. An input signal is produced, stored in an analog or digital processor and that level then becomes the baseline or threshold because of the modification of the gain in the detection circuitry.

A trigger-generator device 40 receives the comparison signal, which determines whether or not the base line has been exceeded, and then produces an indicator signal 42 to establish that the base line has been exceeded. Trigger-generator device 40 sends a signal 46 to optical source 24 indicating that the base line has been exceeded. Optical source 24 then emits treatment beam 26. This process continues until the base line is not exceeded. Optionally, indicator signal 42 can be an audio device 44 such as Model No. SC628E, commercially available from Mallory.

A suitable detection and amplification device 32 is OP Model 17. Comparator 34 can be a Model No. LM2903 Op Amp. Trigger-generator 40 can be a Model No. CD4538BE. All are commercially from R&D Electronics, San Jose, Calif.

At any time during the procedure, the physician can interrupt treatment beam 26 by activating enabling switch 22. This provides great flexibility. The base line can be exceeded but the physician may notice something at treatment site 28 which requires him to deactivate optical source 24. This is readily achieved with enabling switch 22, positioned conveniently at the exterior of cannula 11.

Optical source 24 can be separated into a treatment beam source 24 and a probe beam source 48 (FIG. 4). Probe beam source 48 can be a HeNe or a diode laser such as a HeNe, green, yellow, red, orange, Model No. 1125 MP, commercially available from Uniphase. Alternatively, probe beam source 48 can also be a diode laser, such as diode laser Model No. 9424, commercially available from Toshiba. Different colored probe beams can be used. A green probe beam is excellent for hemoglobin absorption. A red probe beam is useful in treating hair follicles. Changing probe beam 37 is one way of providing different applications of dermatology handpiece 10. However, greater contrast with hemoglobin is obtained with a green probe beam because of absorption characteristics. Treatment beam source 24 can be a KTP 532/1064 laser commercially available from Laserscope, San Jose, Calif. Its output characteristics are 0.5 to 40 watts of 532 nm, 5 watts to 100 watts of 1064 nm at exposure time levels of about 0.01 seconds when operated in the cw mode.

As shown in FIG. 5 treatment beam source can be either a cw laser 24(a) or a pulsed laser 24(b). Both lasers can be incorporated in the same system, or either one can be employed. When cw laser 24(a) is utilized a shutter box and beam dump 50 is also included. This is achieved, in one embodiment, with treatment beam source 24 operating in a lo RF mode on the internal Q-switch, permitting small leakage of light in the form of probe beam 27. The Q-switch acts as a shutter and suppresses the cavity of laser 24(a) from lasing completely. Treatment beam 26 and probe beam 27 can be modulated in order to increase the signal to noise ratio and permit operation in ambient light.

Referring now to FIGS. 6 and 7, a lens 52 is positioned adjacent to dermatology delivery device 12 at its distal end 54 nearest distal end 18 of cannula 11. Lens 52 may be made to vary the spot size from 25 microns to about 5 mm. In one embodiment, lens 52 has a focal length of about 15 mm, and cannula 11 can be adjusted up and down to vary spot size. A spot size of about 25 microns to 5 mm can be produced at treatment site 28.

Detection and amplification device 32 can be an IR detector coupled with an amplifier. A suitable device is Model No. DT 25, commercially available from EG&G. Detection and amplification device 32 is positioned preferably within the cannula 11, so that it looks where probe beam 27 is projected and detects not only total scatter at treatment site 28, but also at the spot where probe beam 27 is projected. In one embodiment, detection and amplification device 32 is approximately 20 degrees off from the optical axis of probe beam 27.

Ambient light can interfere with reflectance/remittance signal 30. To overcome the interference probe beam 27 can be modulated at a frequency above normal background ambient light. This may be, in one example, about 60 Hz. Detection and amplification device 32 can include a high pass filter to remove all of the light except that of probe beam 27.

Additionally, a notch filter can also be used. A suitable one is green notch filter available from Burleigh. With either element the physician can visually see probe beam 27 through window 20 (FIG. 1) without interference from ambient light.

Incorporated within distal end 18 of cannula 11 is a sensor 58 which detects motion of cannula 11. This provides another indicator to the physician that energy is being delivered to treatment site 28 in a even matter. Sensor 58 can be a an IR detector. It provides feedback as to the relative speed of dermatology handpiece 10 motion, and hence assists in the even distribution of optical energy to treatment site 28.

In one embodiment of the invention, dermatology handpiece 10 is moved by the physician around substantially the entire surface of treatment site 28. In this embodiment it is useful to include sensor 58. In another embodiment, a scanning device 60 is positioned in dermatology handpiece 10, preferably in housing 14.

Additionally, probe beam 27 can scan once across treatment beam 26, and a determination made at comparator 34.

A level of treatment power is then formulated. As the absorption of treatment site 28 increases the power of treatment beam 26 will also increase when probe beam 27 scans across the same location.

Scanning device 60 moves an optical fiber 62 which is coupled to optical source 24. Optical fiber 62 is caused to rotate about an optical axis 64 and deliver energy to tissue site 28. An optical focusing element 66, such as a 100 mm fiber with a 15 mm lens, focuses the optical output from optical fiber at treatment site 28. Connecting and crank systems 68 and 70 respectively work in tandem, imparting a rotational movement of optical fiber 62. Connecting and crank systems 68 and 70 are positioned on a frame 72 that includes a platform 74. A bracket 76 holds optical fiber 62 and is supported by platform 74. Motors 78 and 80 provide the power sources to impart movement of connecting and crank systems 68 and 70, as well as connecting rods 82 and 84. A common joint 86 completes the mechanism for rotating optical fiber 62 about optical axis 64.

Referring now to the circuit diagram of FIG. 9, reflectance remittance signal 30 from treatment site 28 goes into a detector 88 which forms part of detection and amplification device 32. Detector 88 may be an op amplifier. Switch 22, positioned at the exterior of dermatology handpiece 10 allows the electronics to be enabled. In the event that the physician has not activated switch 22 then the electronics will not sense anything. The second element of detection and amplification device 32 is an amplifier 90, preferably an op seventeen op amplifier, that amplifies and in certain instances inverts a signal received from detector 88. Associated with amplifier 90 is in integrated circuit 92. The signal from amplifier 90 is received at comparator 34, another op amp.

Comparator 34 is used by the physician to establish the base line. A potentiometer 94 is used by the physician to determine a base line skin level. Potentiometer 94 is adjusted until an LED 96 is turned on, indicating base line or normal skin color. Once the LED is on the physician turns potentiometer 94 one-quarter to one-half of a turn.

This establishes the base line, or threshold. Whenever the signal from detector 88 drops below a certain threshold, established by comparator 34, trigger generator 40 triggers treatment beam source 24 or it causes the signal to go high. If treatment beam 26 is absorbed by the hemoglobin in the skin, or any kind of treatable tissue, the signal to detector 88 goes low. If it goes sufficiently low enough to a point where the skin threshold is accepted then comparator 34 is activated to a high signal.

A switch 98, positioned on the exterior of dermatologic handpiece 10, permits the physician to turn potentiometer 94 until LED 96 emits light, and then turned back slightly in order to scan over treatment site 28.

When the pulsed laser 24(b) of FIG. 5 is used, a Q-Switch driver circuit, shown generally as 100, provides for the output of a certain length of pulse from pulsed laser 24(b). Circuit 100 turns off detector 88 off for a slightly longer amount of time than the Q-switch of pulsed laser 24(b). Regardless of how long circuit 100 sees reflectance/ remittance signal 30, it will only output a certain length of pulse from pulsed laser 24(b).

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A dermatological treatment system for delivering a treatment beam to a dermatological treatment site, comprising in operative combination:
   a) a handpiece having a housing;
   b) a first substantially monochromatic optical energy source to provide a treatment beam having a first wavelength and intensity sufficient to treat dermatologic lesions and other abnormalities;
   c) a second substantially monochromatic optical energy source to generate a probe beam having a second wavelength appropriate to detect dermatologic lesions and other abnormalities as characterized by differences in reflected light intensity when said probe beam is reflected from such lesions and other abnormalities as compared to normal skin tissue, said probe beam and treatment beam able to operate simultaneously;
   e) an optical delivery device having an output end positioned in the housing, the optical delivery device optically connected to said first optical energy source for receiving the treatment beam from said first optical energy source and conducting said treatment beam toward said treatment site;
   f) said optical delivery device is optically connected to said second optical energy source for receiving said probe beam from said second optical energy source and conducting said probe beam toward said treatment site, said probe beam impinging on an area substantially coincident with said treatment beam; and
   g) a treatment beam selectivity means in cooperative electrical connection with said first optical energy source for identifying dermatological abnormalities by directly detecting variations in intensity of reflected light from said probe beam, comparing the intensity of the reflected light with the predetermined threshold level and enabling or disabling said treatment beam in accordance with a predetermined reflected light threshold level.

2. A dermatological treatment system as in claim 1, wherein the treatment beam selectivity device includes a beam contrast means to determine a difference between the treatment beam and the reflectance beam.

3. A dermatological treatment system as in claim 1, wherein at least one of said first and said second optical sources is a laser diode.

4. A dermatological treatment system as in claim 1, said treatment beam selectivity means includes:
   a) a photodetector, for detecting light from said probe beam reflected from said treatment site, to generate a detected reflected light signal;
   b) a comparator, responsive to said detected reflected light signal, for measuring a difference between said detected reflected light signal and a predetermined threshold signal level to produce a comparison signal; and
   c) a trigger generator, responsive to the comparison signal, the trigger generator being electrically coupled to said first optical energy source and enabling the treatment beam when the comparison signal has a predetermined magnitude.

5. A dermatological treatment system as in claim 4, wherein the detector further comprises an amplifier.

6. A dermatological treatment system as in claim 4, further comprising a threshold signal adjustment device coupled to the comparator.

7. A dermatological treatment system as in claim 4, further comprising an indicator signal device coupled to the trigger generator, the indicator signal device producing a discernable signal indicative of the treatment beam.

8. A dermatological treatment system for treating a dermatological target site, comprising:
   a) an optical energy source having at least two different substantially monochromatic wavelengths simultaneously available therefrom, a first wavelength to provide a treatment beam having a wavelength and intensity sufficient to treat dermatologic lesions and other abnormalities, and a second wavelength to provide a probe beam having a wavelength appropriate to detect dermatologic lesions and other abnormalities as characterized by differences in reflected light intensity from such dermatologic lesions or abnormalities as compared to normal skin tissue, said treatment beam being enabled according to the reflected light level of said probe beam;
   b) an optical delivery device, coupled to said optical energy source, to deliver said probe beam and said treatment beam to the target site, means in said optical delivery device to direct said probe beam and said treatment beam to be substantially coincident at the dermatological target site;
   c) a photodetector, for directly detecting reflected light from said probe beam, to generate a detected reflected light signal;
   d) a comparator, responsive to the detected reflected light signal, to measure a difference between the detected reflectance signal and a predetermined threshold signal and produce a comparison signal; and
   h) a trigger generator in cooperative electrical connection with said optical energy source, responsive to the comparison signal to produce a treatment signal when the comparison has a predetermined magnitude thereby enabling said optical energy source to produce a treatment beam.

9. A dermatological treatment system for treating a dermatological target site with a treatment beam of optical energy, comprising:
   a) a handpiece having a housing;
   b) a first substantially monochromatic optical energy source to provide a treatment beam having a wavelength and intensity sufficient to treat dermatologic lesions and other abnormalities;
   c) a second substantially monochromatic optical energy source to generate a probe beam having a wavelength appropriate to detect dermatologic legions and other abnormalities as characterized by differences in reflected light intensity when said probe beam is reflected from lesions and other abnormalities as compared to normal skin tissue;
   d) a first optical delivery device terminating in said housing and optically connected to said first optical energy source for receiving the treatment beam from said first optical energy source and conducting said treatment beam to the treatment site;
   e) a second optical delivery device terminating in said housing and optically connected to said second optical energy source for receiving said probe beam from said second optical energy source and conducting said probe beam to the treatment site, said probe beam impinging on an area of the treatment site substantially coincident to said treatment beam;

f) a photodetector, for directly detecting reflected light from said probe beam, to generate a detected reflected light signal upon detection thereof;

g) a comparator, responsive to the detected reflected light signal, to measure a difference between the detected reflected light signal and a predetermined threshold signal and produce a comparison signal; and h) a trigger generator in cooperative electrical connection with said first optical energy source, responsive to the comparison signal, to produce a treatment signal when the comparison signal has a predetermined magnitude, thereby enabling said first optical energy source to produce a treatment beam.

* * * * *